United States Patent [19]
Wallis

[11] Patent Number: 5,236,417
[45] Date of Patent: Aug. 17, 1993

[54] CHOLANGIOGRAPHY CATHETER APPARATUS AND METHOD

[75] Inventor: William D. J. Wallis, West Valley City, Utah

[73] Assignee: Utah Pioneer Medical, Inc., West Valley City, Utah

[21] Appl. No.: 948,679

[22] Filed: Sep. 22, 1992

[51] Int. Cl.⁵ .................. A61M 25/00; A61B 6/00
[52] U.S. Cl. ........................ 604/82; 604/49; 604/164; 604/247; 604/280; 604/284; 128/655; 128/658
[58] Field of Search ........ 604/49, 53, 82, 83, 604/164, 167, 247, 256, 264, 280, 281, 283, 284; 128/655, 656, 658

[56] References Cited

U.S. PATENT DOCUMENTS

| | | | |
|---|---|---|---|
| 3,399,668 | 9/1968 | Lundgren | 128/655 |
| 3,977,403 | 8/1976 | Patel | 604/280 |
| 4,044,757 | 8/1977 | McWhorter et al. | 128/655 |
| 4,044,758 | 8/1977 | Patel | 128/655 |
| 4,547,187 | 10/1985 | Kelly | 604/284 |
| 4,560,378 | 12/1985 | Weilland | 604/256 |
| 4,795,426 | 1/1989 | Jones | 604/164 |
| 4,867,742 | 9/1989 | Calderon | 128/655 |
| 4,915,688 | 4/1990 | Bischof et al. | 604/83 |
| 4,919,651 | 4/1990 | Doane | 128/656 |

Primary Examiner—John D. Yasko
Assistant Examiner—Anthony Gutowski
Attorney, Agent, or Firm—J. Winslow Young

[57] ABSTRACT

A cholangiography catheter for injecting dye into a cystic duct during laparoscopic cholangiography. The catheter includes a bifurcated connector having a length of tubing and a check valve mounted to each arm of the connector. A saline syringe is coupled to one check valve and a dye syringe is coupled to the other check valve. The check valves and respective syringes are color coordinated to preclude inadvertently using the wrong syringe. The catheter is fabricated from a medical grade polymer having a preselected degree of compliant memory and includes indicia for providing a visual indication of the depth of penetration of the tip of the catheter into the cystic duct.

19 Claims, 2 Drawing Sheets

CHOLANGIOGRAPHY CATHETER APPARATUS AND METHOD

BACKGROUND

1. Field of the Invention

This invention relates to laparoscopic surgical techniques for laparoscopic cholecystectomy and, more particularly, to a novel cholangiography catheter apparatus and method for introducing a liquid contrast medium or dye into the cystic duct during a laparoscopic cholecystectomy.

2. Disclosure Document

This patent application is based, in part, on the subject matter disclosed in Disclosure Document No. 294,219 filed 15 Oct. 1991.

3. The Prior Art

Gallbladder disease is indicated by the presence of gall stones which are caused by the concentration of bile into stones. Bile, constituted primarily of bile salts, is secreted by the liver through ducts into the intestine where it aids in the digestion of fats. Bile is stored and concentrated in the gallbladder where it is available when the digestive processes require additional bile. The common bile duct is formed by the junction of the cystic duct and the hepatic ducts draining from the liver. The bile passing through the bile duct empties into the duodenum adjacent the outlet of the stomach.

It is presently unclear as to what causes gall stones to form, but it has been postulated that infection or a chemical disturbance in the gall bladder may cause gall stones to precipitate from the bile. These gall stones create obstructions to the passage of bile through the ducts and into the intestinal tract. A stone blocking the cystic duct may cause acute inflammation of the gall bladder leading to poor filling and emptying and even loss of function of the gall bladder.

The standard treatment of cholelithiasis (presence of stones in the gallbladder or bile ducts) in the United States is surgical removal of the gallbladder. Historically, this was considered as a major surgical procedure involving a lengthy stay in the hospital and was, therefore, a major economic impact on the patient due to the major surgery, lengthy hospitalization, and absence from work for several weeks.

Choledochotomy, the surgical incision of the common bile duct, should be made if gall stones are present in the duct. Cholangiography aids in identifying the presence of stones and related problems. Also cholangiography may avoid an unnecessary choledochotomy since both the surgical incision of the common duct and the presence of unlocated stone particles may cause post-cholecystectomy morbidity. These unlocated stone particles may become the nucleus of new stones, requiring subsequent surgical intervention. Cholangiography, therefore, aids in the X-ray identification and location of stone particles for their immediate removal.

More than a half million patients underwent total cholecystectomy in 1988, and with the increasing number of elderly patients, this number is expected to increase. Laparoscopic cholecystectomy was developed in an attempt to reduce the morbidity and cost of gallbladder disease by providing a minimally invasive approach to the surgical removal of the gallbladder. The first laparoscopic cholecystectomy was performed in France in 1987 by a gynecologist. By the Fall of 1988 this procedure was being performed clinically. Subsequently, the introduction of and pioneering techniques for laparoscopic cholecystectomy were being performed by Dr. Eddie Joe Reddick and Dr. Douglas Ole Olsen in the United States, and the results thereof are widely reported in the scientific literature. They reported that their techniques allowed for the same day or next day discharge of the patient from the hospital coupled with an expeditious return to full working schedule. As an added benefit, there is minimal scarring from the procedure, making it desirable from a cosmetic standpoint.

Patient acceptance, in fact, demand, for laparoscopic cholecystectomy has been phenomenal with the result that it has become the procedure of choice in treating gallbladder disease. There are many reasons for its popularity. Cosmetically, the four small incisions required for the procedure ar preferred to the large, right subcostal incision of traditional surgery. Pain is minimal. The new procedure allows the patient to be discharged the same day of surgery instead of a several day hospitalization. Most patients can return to work and resume vigorous activity by one week instead of six weeks. Time lost from work and other activities is minimized. Therefore, the economic benefits are two fold: (1) lower hospitalization costs, and (2) reduced loss of employment.

However, with the advent of laparoscopic cholecystectomy, the ability to perform cholangiography has been rendered difficult due to the techniques and equipment employed for the laparoscopic procedure. One currently used prior art technique involves a rigid, stainless steel catheter having an angled tip that is passed through a trocar sleeve in the abdominal wall which is the access port used by the surgeon for instrument access. The angled tip is inserted into the cystic duct and secured with a clip. A syringe containing saline solution is attached to the proximal end of the catheter and is used to flush saline into the common bile duct, possibly indicating whether the common duct is open or blocked. The saline syringe is then replaced with a syringe containing dye or, rather, a contrast medium. The contrast medium is injected into the duct system and an X-ray is taken to identify the presence and location of any stones.

This prior art technique is fraught with a number of problems such as the risk of cystic duct tearing by the rigid catheter, air entry when the syringes are changed, and obscuration of details by the non-radiolucent nature of the stainless steel. An even further problem is that the catheter is inserted through the instrument port so that this port is unavailable to the surgeon for other instrumentation while the catheter is in place. The alternative would be to create a separate access port for the catheter, but this is unacceptable since it represents another incision that requires attention and adds to the healing burden of the patient.

Another prior art technique was to use a ureteral catheter cut immediately behind the side ports. This catheter had the advantages of being flexible and radiolucent. However, it has no Luer fitting for securing the saline and dye syringes and the sharp edge resulting from its fenestrated tip being cut off is a cause for concern. There is still the risk of air entering the catheter when the syringes are changed. Also, there is no way for telling how far the catheter has been inserted into the cystic duct. The softness of the catheter may also allow it to become occluded when the clip is applied to secure the catheter to the cystic duct.

In view of the foregoing, it would be an advancement in the art to provide a cholangiography catheter apparatus and method for delivering contrast media to a cystic duct that is easy to implement, safer to use, and eliminates guess work as to its depth of penetration in the cystic duct. Another advancement in the art would be to provide a cholangiography catheter having a connector system for accommodating the simultaneous coupling of both a saline syringe and a contrast medium syringe to the cholangiography catheter. Another advancement in the art would be to provide a cholangiography catheter that is sufficiently pliant to allow it to be bent into predetermined curvature but with sufficient stiffness to resist being occluded when the clip is applied. Another advancement would be to provide an access port for admitting a guide wire into the catheter to thereby enable the surgeon to utilize the guide wire during the surgical procedure. Another advancement would be to provide cholangiography catheter having indicia on the distal end to provide an indication of the depth of insertion of the catheter tip into the cystic duct. Another advancement would be to provide a cholangiography catheter that can be inserted through a simple puncture in close proximity to the cystic duct and without interfering with the surgeon's access to the instrument port. It would also be an advancement to provide a cholangiography catheter having minimal slipperiness when wetted by body fluids to thereby more readily facilitate maintenance of the insertion depth of the tip of the catheter in the cystic duct. Such a novel invention is disclosed and claimed herein.

BRIEF SUMMARY OF OBJECTS OF THE INVENTION

This invention relates to a novel cholangiography catheter apparatus and method for use during laparoscopic surgery to introduce a contrast medium into the cystic duct. The catheter includes a connector for coupling two syringes to the catheter. One syringe is filled with saline and the other syringe is filled with the contrast medium. Color coordinated, one-way valves control the flow of liquid from each syringe. The connector also includes an access port for introducing a guide wire into the catheter. The catheter has a predetermined degree of compliant memory to enable the surgeon to form and retain a preselected curvature in the catheter after passage of the catheter through the abdominal wall. Marks on the tip of the catheter provide an indication of the depth of penetration of the catheter tip into the cystic duct.

It is, therefore, a primary object of this invention to provide improvements in cholangiography catheters.

Another object of this invention is to provide improvements in the method of introducing a contrast medium into the cystic duct during a laparoscopic cholecystectomy.

Another object of this invention is to provide a cholangiography catheter having both the contrast medium syringe and the saline syringe, each syringe being releasably connectable to the catheter through one-way valves.

Another object of this invention is to provide a cholangiography catheter having a catheter fabricated from a conformable, radiolucent plastic having a thin, radiopaque stripe along its length.

Another object of this invention is to provide a connector for unidirectionally coupling the contrast medium syringe and the saline syringe to the catheter.

Another object of this invention is to provide the connector with an access port for introducing a guide wire into the catheter.

Another object of this invention is to provide indicia on the tip of the cholangiography catheter as a visual indicator of the depth of insertion of the tip into the cystic duct.

Another object of this invention is to provide a cholangiography catheter that can be inserted through a simple puncture in the abdominal wall in close proximity to the cystic duct.

Another object of this invention is to provide a cholangiography catheter having minimal wall slipperiness when wetted by body fluids to facilitate security when handling and maintenance of the insertion depth when the tip of the catheter is inserted in the cystic duct.

These and other objects and features of the present invention will become more readily apparent from the following description in which preferred and other embodiments of the invention have been set forth in conjunction with the accompanying drawing and appended claims.

DETAILED DESCRIPTION OF THE PREFERRED EMBODIMENT

Figure 1:
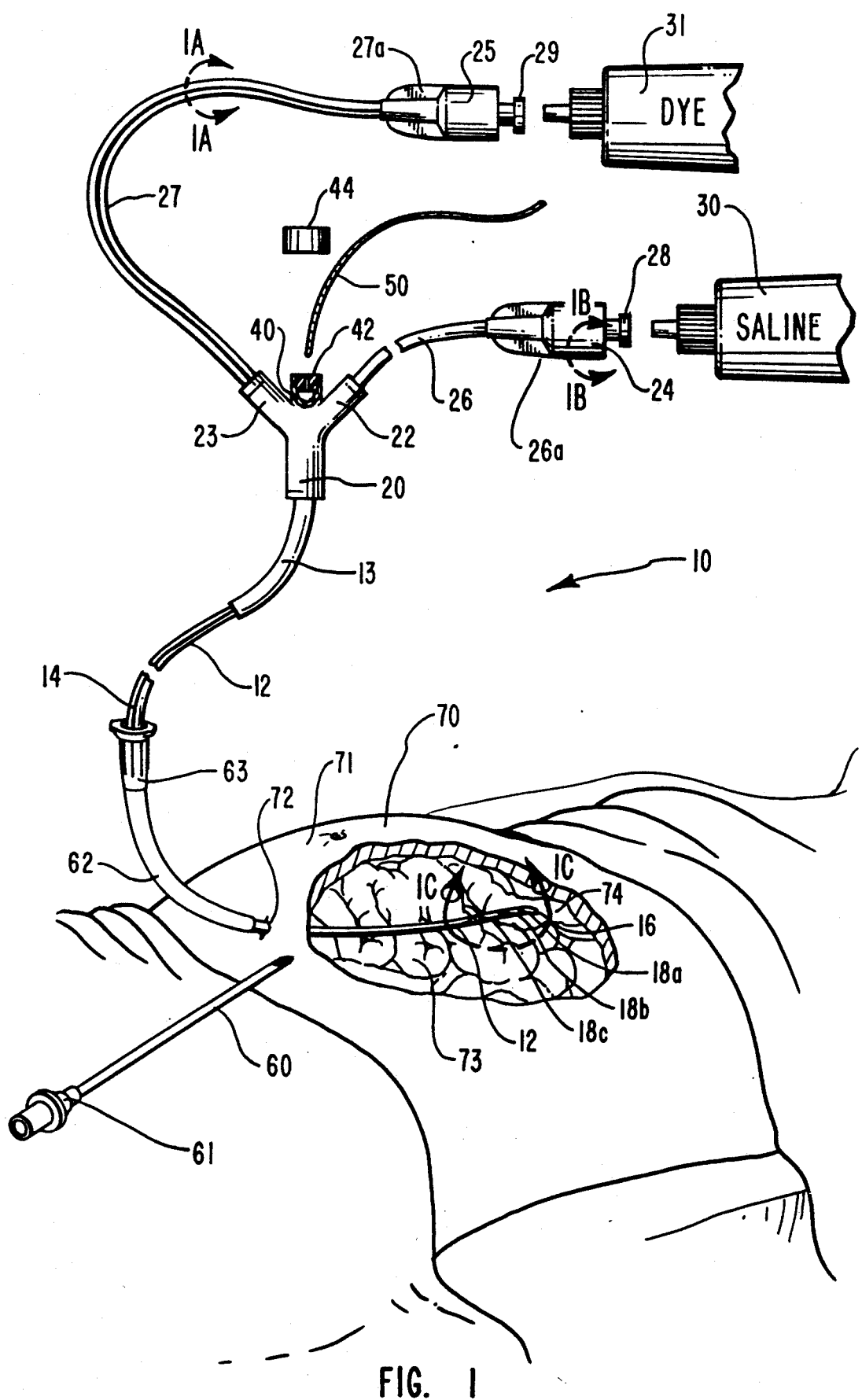
FIG. 1 is a perspective view of the novel cholangiography catheter of this invention shown in the environment of a patient undergoing laparoscopic cholecystectomy with portions broken away to reveal underlying features.

The invention is best understood by reference to the drawing wherein like parts are designated by like numerals throughout in conjunction with the following description and appended claims.

GENERAL DISCUSSION

This invention incorporates a number of unique features to provide a novel cholangiography catheter. An introducer is also provided as a mechanism for inserting the catheter through the abdominal wall in a sealing relationship. The catheter includes a single lumen catheter extending from a bifurcated connector. The tip of the single lumen catheter is marked with a series of indicia to provide a visual indication of the depth of insertion of the catheter tip into the cystic duct. The bifurcated connector has a one-way valve incorporated into each arm of the connector. Two pieces of tubing (one of which is color coded) of unequal length extend from the connector to one-way valves to which are mounted female Luer connectors. Color coded and labeled syringes are provided for interconnection to the Luer connectors. One syringe is labelled in black lettering with the word "SALINE" to be used as the irrigation medium. The other syringe is labelled in blue lettering with the word "DYE" to be used as the contrast medium. The color coding assures that the proper syringe is coupled to the correct tubing and is properly used by the surgeon during the surgical procedure. All of the liquid handling components of the catheter including the syringes, tubing, connector, and the catheter itself are fabricated from a clear or at least translucent material so to reveal the presence of air bubbles.

The introducer includes a flexible sheath releasably mounted to a sharpened needle or trocar. The needle is used to penetrate the abdominal wall and carry the sheath through the abdominal wall after which the needle is withdrawn leaving the sheath in place as the port through which the catheter is inserted. After insertion of the catheter the sheath is retracted up the length of the catheter where it is retained out of the way. The abdominal wall is then free to sealingly engage the catheter in a sealing relationship.

DETAILED DESCRIPTION

Referring now more particularly to FIG. 1, the novel cholangiography catheter of this invention is shown generally at 10 and includes a catheter 12 extending from a connector 20. Cholangiography catheter 10 is shown greatly enlarged in the environment of a patient 70 with catheter 12 passed through abdominal wall 71 at a puncture 72 and into contact with a cystic duct 74. The underlying intestines 73 are shown schematically to further illustrate the environment of catheter 12 in relation to cystic duct 74. Catheter 12 is fabricated from a clear polyvinylchloride (PVC) plastic and has a radiopaque stripe 14 along its length from connector 20 to a tip 16. A plurality of indicia 18a–18c (FIG. 1C) adjacent tip 16 provide a visual indication of the depth of insertion of tip 16 into the cystic duct 74. In this instance, indicia 18a is shown as a single stripe, indicia 18b as a double stripe, and indicia 18c as three stripes thereby providing a clearly readable and readily understandable indication of how far tip 16 has been inserted into cystic duct 74.

The PVC of catheter 12 imparts a preselected degree of conformability to catheter 12 so that the surgeon (not shown) can deformably shape the curvature of tip 16 prior to passing it through puncture 72 and have tip 16 retain the preset curvature. This enables the surgeon to readily insert tip 16 into a small hole snipped in cystic duct 74 and to a depth indicated by indicia 18a–18c. The PVC has another advantage in that it has sufficient rigidity to resist collapse when it is sealingly clamped to cystic duct 74 after insertion. A further advantage to the medical grade PVC from which catheter 12 is fabricated is that it provides minimal slipperiness when wetted by body fluids and thereby is more easily maintained in its preselected depth of insertion into cystic duct 74 when secured thereto with a clip (not shown) according to current practice.

The length of catheter 12 is sufficient to allow connector 20 to be placed a suitable distance away from puncture 72 and cystic duct 74 so that it does not interfere with the various other instruments (not shown) being used during the surgical procedure. I have found that a length of about 30 inches (70 cm) is entirely suitable for these purposes. However, it should be noted that puncture 72 is generally located in close proximity to cystic duct 74 for easier, more direct placement of catheter tip 16 in cystic duct 74. As shown, puncture 72 is removed from cystic duct 74 in order to more readily show the interrelationship of the various components of this invention. The selective placement of puncture 72 also provides the distinct advantage in that it eliminates entirely the passage of catheter 12 through the conventional instrument port (not shown) thereby precluding any interference with the instruments (not shown) inserted therethrough.

Figure 1A:
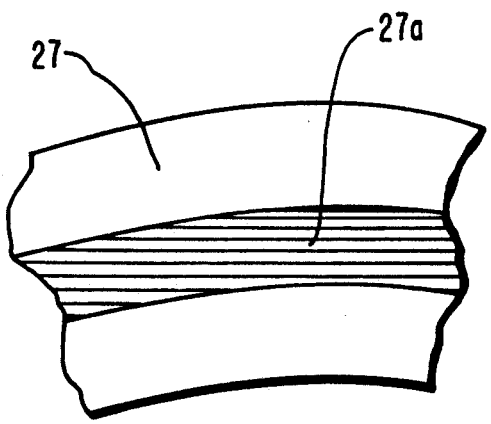
FIG. 1A is a fragmentary enlargement of the dye tubing to illustrate that the dye tubing is marked with a blue stripe.
Figure 1B:
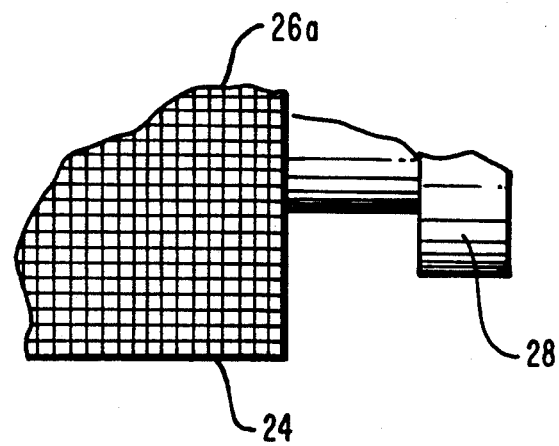
FIG. 1B is a fragmentary enlargement of the saline check valve to illustrate that the saline check valve is marked black.
Figure 1C:
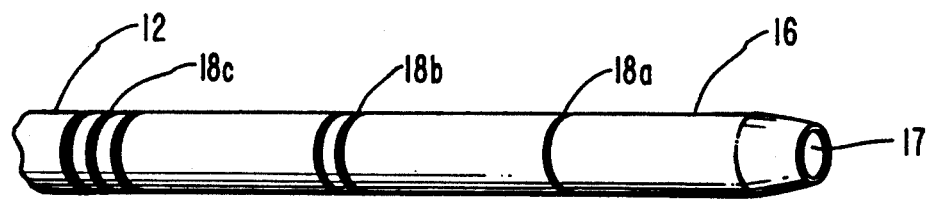
FIG. 1C is a fragmentary enlargement of the distal tip of the catheter.

Connector 20 is mounted to catheter 12 through a strain relief 13 and includes a saline arm 22 and a dye arm 23. Saline arm 22 has a normally closed check valve 24 mounted thereto while dye arm has a normally closed check valve 25 mounted thereto. A tubing 26 is coupled at one end to saline arm 22 and terminated at the other end in a black color coded (see FIG. 1B) check valve 24 to which is affixed a Luer fitting 28. Correspondingly, a blue color coded (see FIG. 1A) tubing 27 is coupled at one end to dye arm 23 and terminated at the other end in a blue color coded check valve 25 to which is affixed a Luer fitting 29. The color coding of black color coded check valve 24 is best seen in the fragmentary enlargement at FIG. 1B while the color coding of blue color coded tubing 27 is best seen in the fragmentary enlargement at FIG. 1A wherein the blue stripe therein is shown at 27a. The color coding used in FIGS. 1A and 1B is that used to illustrate colors in an application for registration of a trademark. Check valve 24 is also color coded black as indicated by black color 26a while both the stripe in tubing 27 (FIG. 1A) and check valve 25 is color coded blue as indicated by blue color 27a. In addition to being separately color coded, tubing 26 is incrementally shorter than tubing 27. In this first preferred embodiment of the invention, tubing 26 is about four inches (10 cm) long while tubing 27 is about five inches (13 cm) long. This allows the syringes to rest side by side in an incrementally offset manner.

Another purpose for having a noticeable difference in the respective lengths of tubing 26 and 27 is to provide a system for enabling the medical technician (not shown) to distinguish between the two tubings, tubing 26 and 27, particularly under the low level light conditions commonly found surrounding the periphery of the surgical field. To further assist the medical technician tubing 27 includes a distinctive stripe of color 27a along its length whereas tubing 26 does not have a stripe. In this way the medical technician is provided a second system for assuring that the correct syringe, syringes 30 and 31 are activated correctly during the foregoing procedure. For example, color 26a is shown as the light conditions blue color 27a can easily be confused with black color 26a so that with only one tubing, tubing 27, marked with the stripe of blue color 27a it is nearly impossible to confuse tubing 27 with tubing 26.

Color coded syringes are selectively coupled to Luer fittings 28 and 29. In this embodiment of the invention, a saline syringe 30 is marked in black lettering with the word "SALINE" while a dye syringe 31 is marked in blue lettering with the word "DYE." Each syringe is configured as a conventional 20 cc syringe suitable for holding and injecting the respective liquid therein.

Check valves 24 and 25 are normally closed and open under pressure from syringes 30 and 31, respectively, to allow the respective fluids therein to enter catheter 12. For example, pressure on syringe 30 will force the saline therein to open check valve 24 to allow the saline to enter tubing 26 and catheter 12. Check valve 25 prevents the reverse flow of saline into syringe 31. Correspondingly, pressure on syringe 31 forces dye through check valve 25 into tubing 27 and catheter 12. Check valve 24 prevents the reverse flow of dye into syringe 30.

Connector 20 includes an access port 40 having a sliding seal 42 therein and enclosed by a cap 44. Sliding seal 42 is a conventional sliding seal and is configured to allow the passage of a guide wire 50 into catheter 12. This is done by removing cap 44 and passing the tip of guide wire 50 through sliding seal 42 with sliding seal 42 sealingly closing access port 40 against fluid loss while at the same time allowing guide wire 50 to be directed into catheter 12.

The introducer for catheter 12 is a conventional introducer and is shown as a sharp pointed needle 60 having a flexible sheath 62 slidably mounted thereto. Needle 60 extends from a needle hub 61 while flexible sheath 62 extends from a sheath hub 63. Needle 60 is configured as a conventional catheter introducer such that when needle 60 forms puncture 72 through abdominal wall 71 it carries sheath 62 through abdominal wall 71. Thereafter, sheath hub 63 is held firmly in place against abdominal wall 71 while needle hub 61 is grasped and pulled to remove needle 60. Needle 60 is then discarded in a suitable receptacle. Sheath hub 63 now serves as a receiver for tip 16 when it is time to insert catheter 12 through abdominal wall 71. Thereafter sheath hub 63 is grasped and sheath 62 is retracted up the length of catheter 12 to a position adjacent strain relief 13 on connector 20 where sheath 62 is effectively out of the way of the ongoing surgical procedure.

THE METHOD

At the beginning of the surgical procedure using cholangiography catheter 10, the medical professional (not shown) assisting the surgeon (not shown) obtains cholangiography catheter 10 and attaches thereto syringe 31 which has been prefilled with the desired contrast medium. With syringe 31 securely mated to Luer fitting 29, the length of tubing 27 and dye arm 23 are charged with the contrast medium. Saline is then drawn into syringe 30 and syringe 30 is then securely mated to Luer fitting 28. Tubing 26, saline arm 22, and catheter 12 are then flushed with saline to remove all remaining air from cholangiography catheter 10.

The surgeon (not shown) then obtains needle 60 having sheath 62 slidably mounted thereon with sheath hub 63 in abutment with needle hub 61. The sharpened point of needle 60 is pressed against abdomen 71 at the preselected location in the vicinity of cystic duct 74 and pierced therethrough at puncture 72 created thereby. Sheath hub 63 is held against abdomen 71 while needle hub 61 is grasped and pulled to retract needle 60 leaving sheath 62 in place in puncture 72. Catheter 12 is then threaded through the hollow lumen of sheath 62 until catheter tip 16 thereof can be grasped by the surgeon and directed into the proper location at cystic duct 74. Sheath 62 is withdrawn from puncture 72 and slidably retracted up catheter 12 until it reaches the vicinity of strain relief 13 where it is held out of the way for the ongoing procedure. The tissue of abdominal wall 71 surrounding puncture 72 sealingly encloses catheter 12 in a leakproof relationship to prevent the loss of gas from abdomen 71. Needle 60 is no longer required and may be discarded according to conventional practice.

Catheter tip 16 is inserted into cystic duct 74 with indicia 18a-18c providing a visual indication of its depth of insertion. Thereafter, catheter 12 is sealingly clipped to cystic duct 74 to prevent leakage. The contrast medium is expelled through the hollow end 17 of catheter tip 16 (FIG. 1C) where it is directed into cystic duct 74 for the cholangiography analysis of cystic duct 74.

In the event the surgeon (not shown) encounters a blockage or other abnormality in cystic duct 74 requiring the use of a guide wire, guide wire 50 (shown fragmentarily herein) is directed through sliding seal 42 until the tip thereof exits hollow end 17. Accordingly, catheter 12 not only selectively provides a saline flush from syringe 30 and a supply of contrast medium from syringe 31 but also mechanical device for mechanically probing cystic duct 74 by the judicious use of guide wire 50.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A catheter apparatus for laparoscopic cholangiography comprising:
   a catheter having a distal end and a proximal end, said distal end being suitable for incremental insertion into the cystic duct of a patient, said catheter comprising a preselected length sufficient to pass through the abdominal wall of said patient to said cystic duct from a position external of said patient, said catheter comprising a set of indicia at said distal end and a radiopaque line along said preselected length;
   an introducer for introducing said catheter through said abdominal wall;
   a connector mounted to said proximal end of said catheter, said connector comprising a first interconnect for introducing saline solution into said catheter and a second interconnect for introducing dye into said catheter;
   a first tubing connected at a distal end to said first interconnect;
   a first check valve mounted to a proximal end of said first tubing;
   a first syringe removably mountable to said first check valve, said first syringe containing saline for introducing said saline into said catheter;
   a second tubing connected at a distal end to said second interconnect;
   a second check valve mounted to a proximal end of said second tubing; and
   a second syringe removably mountable to said second check valve; said second syringe containing dye for introducing said dye into said catheter.

2. The catheter apparatus defined in claim 1 wherein said indicia on said distal end of said catheter comprise. discrete sets of bands around said catheter at sequentially spaced intervals from said distal end, a first set of bands from said distal end comprising a single band, a second set of bands adjacent said first set of bands comprising two bands, and a third set of bands adjacent said second set of bands comprising three bands.

3. The catheter apparatus defined in claim 1 wherein said connector comprises a third interconnect on said connector for introducing a guide wire into said catheter.

4. The catheter apparatus defined in claim 1 wherein said first check valve is color coordinated with said first syringe using a first color and said second check valve is color coordinated with said second syringe using a second color.

5. The catheter apparatus defined in claim 1 wherein said catheter comprises a medical grade polymer comprising a preselected degree of wall stiffness to resist crushing when said distal end is clamped to said cystic duct.

6. The catheter apparatus defined in claim 5 wherein said polymer comprises a preselected degree of compliant memory to accommodate said catheter being capable of retaining a preselected degree of curvature.

7. The catheter apparatus defined in claim 5 wherein said medical grade polymer comprising PVC having a preselected degree of minimal slipperiness to facilitate maintenance of said catheter tip at a predetermined insertion depth.

8. A cholangiography catheter for use during laparoscopic surgery comprising:
a catheter comprising a radiolucent, medical grade plastic, said plastic comprising a compliant memory, said catheter comprising a distal end and a proximal end, said distal end comprising indicia to provide a visual indication of the depth of insertion of said distal end;
a connector coupled in fluid communication to said proximal end of said catheter, said connector comprising a saline arm and a dye arm;
a saline tubing having a distal end and a proximal end and coupled in fluid communication to said saline arm at said distal end;
a dye tubing having a distal end and a proximal end and coupled in fluid communication to said dye arm at said distal end;
a saline check valve mounted in fluid communication to said proximal end of said saline tubing;
a dye check valve mounted in fluid communication to said proximal end of said dye tubing;
a saline syringe releasably mountable to said saline check valve; and
a dye syringe releasably mountable to said dye check valve.

9. The cholangiography catheter defined in claim 8 wherein said connector includes an access port comprising an opening having a sliding seal and a removable cover for said access port, said access port providing access for a guide wire to be directed into said catheter with said sliding seal providing a sealing relationship between said access port and said guide wire.

10. The cholangiography catheter defined in claim 8 wherein said saline check valve is color coordinated with said saline syringe using a first color and said dye check valve is color coordinated with said dye syringe using a second color.

11. The cholangiography catheter defined in claim 8 wherein said saline tubing comprises a first length and said dye tubing comprises a second length.

12. The cholangiography catheter defined in claim 8 wherein said catheter comprises a radiopaque stripe along its length.

13. A method for introducing a contrast medium to a cystic duct during laparoscopic cholangiography comprising:
obtaining a catheter having a proximal end and a distal end, said catheter comprising a medical grade polymer having a preselected degree of compliant memory;
mounting a connector in fluid communication to said proximal end of said catheter, said connector comprising a saline arm and a dye arm, said saline arm connected in fluid communication to a saline check valve through a saline tubing, said dye arm connected in fluid communication to a dye check valve through a dye tubing;
filling a dye syringe with dye and attaching said dye syringe to said dye check valve and flushing said dye tubing and said dye arm;
filling a saline syringe with saline and attaching said saline syringe to said saline check valve and flushing said saline tubing and said catheter with said saline; and
inserting said distal end of said catheter into said cystic duct and injecting said dye from said dye syringe into said cystic duct.

14. The method defined in claim 13 wherein said obtaining step includes placing indicia on said distal end of said catheter for providing a visual indicator of the depth of insertion of said distal end of said catheter during said inserting step.

15. The method defined in claim 13 wherein said inserting step comprises selectively conforming said distal end of said catheter using said compliant memory prior to inserting said distal end of said catheter into said cystic duct.

16. The method defined in claim 13 wherein said mounting step includes forming an access port in said connector for a guide wire and placing a sliding seal in said access port, said inserting step including introducing a guide wire into said catheter.

17. The method defined in claim 13 wherein said mounting step includes color coordinating said saline check valve with said saline syringe using a first color and said dye check valve with said dye syringe using a second color.

18. The method defined in claim 17 wherein said dye tubing includes a stripe of said second color to distinguish said dye tubing from said saline tubing under low level light conditions.

19. The method defined in claim 13 wherein said inserting step includes providing a sharpened needle and a sheath slidably mounted to said needle, said needle puncturing the abdominal wall and placing said sheath in said abdominal wall, said needle being removable to leave said sheath temporarily in said abdominal wall, said sheath providing an access for passing said catheter through said abdominal wall, and retracting said sheath toward said proximal end of said catheter when said catheter has been inserted through said abdominal wall.

* * * * *